United States Patent [19]

Randolph et al.

[11] Patent Number: 5,450,950
[45] Date of Patent: Sep. 19, 1995

[54] CONDOM DISPLAY AND STORAGE SYSTEM SIMULATING AUDIO CASSETTE DISPLAY AND STORAGE SYSTEM

[76] Inventors: Delbert D. Randolph, Box 191; Gerald E. Wagnon, Rte. 1, Box. 147, both of Great Bend, Kans. 67530

[21] Appl. No.: 222,665

[22] Filed: Apr. 4, 1994

[51] Int. Cl.6 .............................................. B65D 85/08
[52] U.S. Cl. ...................... 206/232; 206/69; 206/457
[58] Field of Search ................ 206/69, 232, 387, 457, 206/526, 534

[56] References Cited

U.S. PATENT DOCUMENTS

| | | | |
|---|---|---|---|
| 1,895,233 | 1/1933 | Rossen | 206/457 |
| 2,332,857 | 10/1943 | Karg | 206/69 |
| 2,797,806 | 7/1957 | Davis | 206/457 |
| 3,272,325 | 9/1966 | Schoenmakers | 206/387 |
| 4,271,961 | 6/1981 | Blankenmeister | 206/387 |
| 4,341,307 | 7/1982 | Shyers | 206/387 |
| 4,368,817 | 1/1983 | Temesvary | 206/387 |
| 4,913,287 | 4/1990 | Kagano | 206/387 |
| 5,064,071 | 11/1991 | Kerfoot, Jr. | 206/534 |
| 5,156,271 | 10/1992 | Toner | 206/457 |
| 5,244,096 | 9/1993 | Stoner | 206/69 |

FOREIGN PATENT DOCUMENTS

| | | | |
|---|---|---|---|
| 3940697 | 6/1991 | Germany | 206/69 |
| 0442835 | 2/1936 | United Kingdom | 206/69 |

Primary Examiner—Jimmy G. Foster
Attorney, Agent, or Firm—John R. Flanagan

[57] ABSTRACT

A condom display and storage system simulates an audio cassette display and storage system which facilitates unobtrusive display of condoms for sale in retail stores and personal storage of condoms at an easily accessible location. The condom display and storage system includes a display and storage case having first and second parts pivotally connected together and movable between opened and closed positions, an insert card received in a shelf of the first part of the case, and a plurality of condom containers stacked within the shelf and insert card of the case.

5 Claims, 1 Drawing Sheet

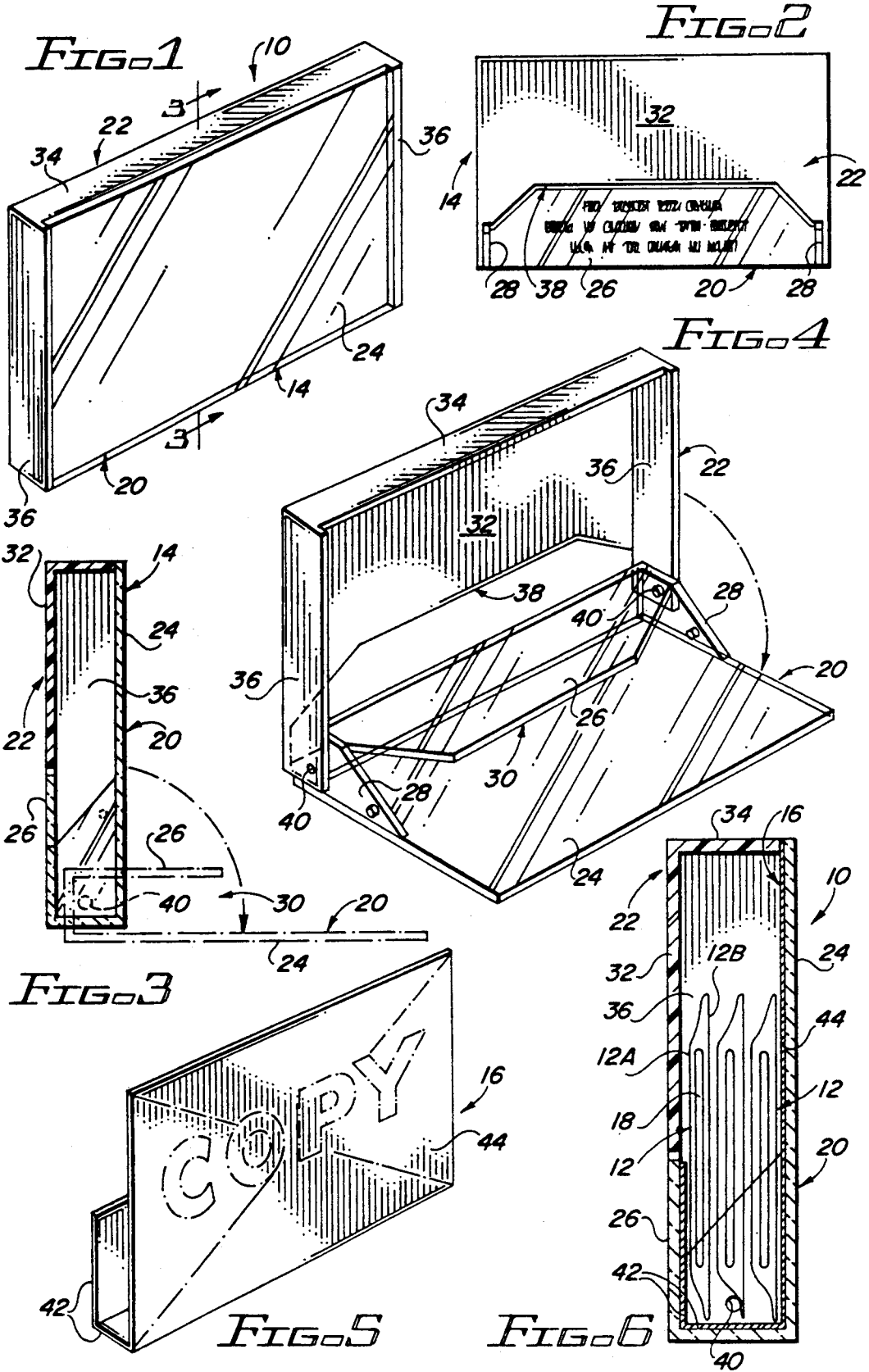

CONDOM DISPLAY AND STORAGE SYSTEM SIMULATING AUDIO CASSETTE DISPLAY AND STORAGE SYSTEM

BACKGROUND OF THE INVENTION

1. Field of the Invention

The present invention generally relates to packaging for retail sale and personal storage of condoms, and, more particularly, is concerned with a condom display and storage system for simulating an audio cassette display and storage system to facilitate unobtrusive display of condoms for sale in retail stores and personal storage of condoms at an easily accessible location.

2. Description of the Prior Art

Heretofore, condoms have typically been distributed and sold in sealed flexible foil wrapped packages or containers having relatively flat rectangular or circular shapes. The flexible foil wrapped containers are typically displayed in cartons or boxes in retail stores and are kept inconspicuously in a drawer or cabinet in the home or in a person's wallet or purse. The flexible foil wrapper container is adapted to be torn open to gain access to the condom.

The advent and spread of Acquired Immune Deficiency Syndrome (AIDS) has heightened public awareness of and concern with the potentially-fatal risks associated with persons having unprotected sexual intercourse. Next to abstinence, condoms have become widely considered to be the next most effective measure to prevent transmission of AIDS. Testimony before the U.S. Congress by an official of the World Health Organization's global program on AIDS announced that widespread distribution of condoms by WHO has partly controlled the spread of AIDS in five areas of the world.

Because of the effectiveness of condoms compared to other viable alternatives, public information programs about AIDS prevention have propelled the subject of condom distribution and use into the arena of public discussion. However, imaginative ways to effectively promote condom purchase and use by high risk population segments as well as the general population are lacking.

Consequently, there is a continuing need for effective techniques to enhance public awareness and acceptance of condoms in the fight against the spread of AIDS.

SUMMARY OF THE INVENTION

The present invention provides a condom display and storage system designed to satisfy the aforementioned needs. The condom display and storage system of the present invention simulates an audio cassette display and storage system so as to facilitate several purposes. One purpose is the unobtrusive display of condoms for sale in a wide variety of retail stores while attracting the attention of the segment of the consumers interested in audio cassette recordings. Another purpose is the personal storage of condoms in open easily accessible locations such as with audio cassette recordings.

Accordingly, the present invention is directed to a condom display and storage system for simulating an audio cassette display and storage system. The condom display and storage system comprises: (a) a display and storage case having first and second parts pivotally connected and movable between opened and closed positions relative to one another; (b) an information-bearing insert card disposed within the case; and (c) a plurality of condom containers removably stacked within one of the first and second parts of the case. The first part of the display and storage case has a transparent wall and a shelf mounted at a rear side of the transparent wall. The second part of the display and storage case is hinged to the first part and pivotally movable between opened and closed positions relative to the rear side of the first part. The insert card has a backstop portion removably seated on the shelf of the first part of the case and a front upright card portion extending in a flush relationship along the transparent front wall thereof. The upright card portion has instructional and graphical indicia printed thereon. The plurality of condom containers are stacked within the shelf of the first part of the case and between the backstop portion and front upright card portion of the insert card.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a front perspective view of a condom display and storage system of the present invention, showing a display and storage case of the system in a closed condition.

FIG. 2 is a rear elevational view of the condom display and storage system.

FIG. 3 is a cross-sectional view of the display and storage case of the system taken along line 3—3 of FIG. 1.

FIG. 4 is a front perspective view of the display and storage case of the system shown in an open condition.

FIG. 5 is a perspective view of a J-shaped information bearing insert employed in the condom display and storage system.

FIG. 6 is an enlarged cross-sectional view of the condom display and storage system having a plurality of flexible foil wrapped condom containers and the J-shaped insert disposed in the display and storage case of the system.

DETAILED DESCRIPTION OF THE INVENTION

Referring to the drawings, and particularly to FIGS. 1 and 6, there is illustrated a condom display and storage system of the present invention, generally designated 10, for simulating an audio cassette display and storage system. Basically, the condom display and storage system 10 includes a plurality of condom containers 12, a display and storage case 14, and an insert card 16. Preferably, each condom container 12 is a tearable hermetically-sealed foil wrapper-type container 12 which is conventional and well-known per se. The condom container 12 preferably has a circular or coin-shaped configuration with front and rear opposite sides 12A, 12B. A condom 18, shown in dashed outline form, in rolled-up condition is stored in a sealed interior chamber of the condom container 12 between its front and rear sides 12A, 12B.

The display and storage case 14 and insert card 16 are substantially the same as ones typically used in the storage of audio cassette tapes except that a pair of internal lugs, which were used for holding the audio tape cartridge in the case when the case is closed, have now been removed from the case 14. The display and storage case 14 has a first part 20 and a second part 22 hinged to the first part 20. The first part 20 of the case 14 has a transparent front wall 24 and a plurality of interconnected back and opposite side walls 26, 28, being shorter in height than the transparent front wall 24 and which define a shelf 30 mounted at a rear side of the front wall 24.

The second part 22 of the case 14 has a rear wall 32 and a plurality of interconnected top and opposite side walls 34, 36 connected to and extending outwardly from the rear wall 32. The rear wall 32 has a cutout region 38 in the same shape as the shelf 30 permitting the rear wall 32 to align with the back wall 26 of the shelf 30.

The first and second parts 20, 22 of the case 14 have complementary detents 40 in the form of interfitting pins and apertures provided at the lower ends of the respective opposite side walls 28 of the first part 20 and at the lower ends of the respective opposite side walls 36 of the second part 22. The complementary detents 40 define a pair of hinges located at opposite sides of the shelf 30 about which the second part 22 is pivotally movable between opened and closed positions relative to the rear side of the first part 20.

The insert card 16 is folded from a flat blank into a backstop portion 42 removably seated on the shelf 30 of the first part 20 of the case 14 and a front upright card portion 44 extending in a flush relationship along the transparent front wall 24 of the first part 20 of the case 14. The front upright card portion 44 has instructional and graphical indicia printed on the front surface 44A thereof which can be seen through the transparent front wall 24 of the first part 20 of the case 16. The plurality of condom containers 12 stacked are within and removable from the shelf 30 of the first part 20 of the case 16 when the second part 22 is opened relative to the first part 20.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

We claim:

1. A condom display and storage system, comprising:
    (a) a display and storage case having first and second parts being pivotally connected and movable between opened and closed positions relative to one another, said first part of said display and storage case having a transparent wall and a shelf mounted at a rear side of said transparent wall, said shelf being configured to receive stacked condoms therein;
    (b) an information-bearing insert card disposed within said case, said insert card having a backstop portion removably seated on said shelf of said first part of said case; and
    (c) a plurality of condom containers removably stacked within said first part of said case, said plurality of condom containers being stacked within said shelf of said first part of said case and between said backstop portion and front upright card portion of said insert card.

2. The system of claim 1 wherein said second part of said display and storage case is hinged to said first part and pivotally movable between opened and closed positions relative to said rear side of said first part.

3. The system of claim 1 wherein said insert card also has a front upright card portion extending in a flush relationship along said transparent front wall of said first part of said case.

4. The system of claim 3 wherein said upright card portion has instructional and graphical indicia printed thereon.

5. A condom display and storage system, comprising:
    (a) a display and storage case having a first part defining a transparent front wall and a shelf mounted at a rear side of said transparent front wall and a second part hinged to said first part and being pivotally movable between opened and closed positions relative to said rear side of said first part, said shelf being configured to receive condoms stacked therein;
    (b) an insert card having a backstop portion seated on said shelf of said first part of said case and a front upright card portion extending in a flush relationship along said transparent front wall of said first part of said case, said upright card portion having instructional and graphical indicia printed thereon; and
    (c) a plurality of condom containers stacked within said shelf of said first part and said insert card of said case.

* * * * *